United States Patent [19]

Horn

[11] Patent Number: 4,885,308

[45] Date of Patent: Dec. 5, 1989

[54] METHOD AND COMPOSITIONS FOR TREATMENT OF PARKINSONISM SYNDROME IN MAMMALS

[75] Inventor: Alan S. Horn, Groningen, Netherlands

[73] Assignee: Nelson Research & Development Co., Irvine, Calif.

[21] Appl. No.: 206,193

[22] Filed: Jun. 13, 1988

Related U.S. Application Data

[63] Continuation-in-part of Ser. No. 640,685, Aug. 13, 1984, Pat. No. 4,564,628, and a continuation-in-part of Ser. No. 811,768, Dec. 20, 1985, Pat. No. 4,657,925.

[51] Int. Cl.$^4$ .......................................... A61K 31/38
[52] U.S. Cl. ..................................................... 514/438
[58] Field of Search ........................ 514/646, 653, 438

[56] References Cited

U.S. PATENT DOCUMENTS

| 4,564,628 | 1/1986 | Horn | 514/438 |
| 4,657,925 | 4/1987 | Horn | 514/438 |
| 4,722,933 | 2/1988 | Horn | 514/438 |

OTHER PUBLICATIONS

U.S. Patent Application Ser. No. 047,882 filed 5/8/87 for Method for Treating Schizophrenia.

Primary Examiner—Stanley J. Friedman
Attorney, Agent, or Firm—Robert J. Baran; June M. Bostich

[57] ABSTRACT

This invention provides a method for treating the symptoms of parkinsonism which comprises administering to a human or other mammal suffering from the symptoms of parkinsonism an effective amount of a compound selected from the group consisting of optically-active or racemic compounds represented by the general formula:

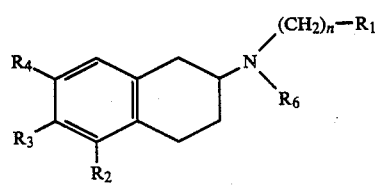

wherein
$R_1$ is selected from the group consisting of organic radicals methyl, substituted or unsubstituted phenyls, pyridyl, hydroxyphenyl,

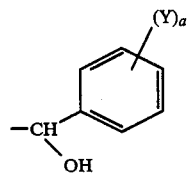

-continued

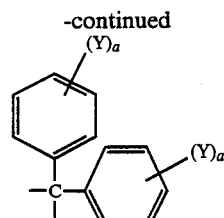

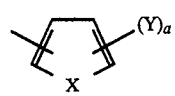

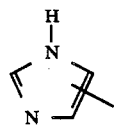

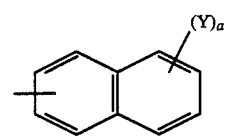

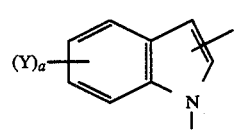

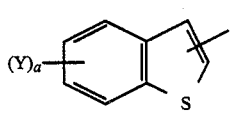

X is oxygen or sulfur,
Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms. and a is an integer of from zero to 3,
$R_2$, $R_3$ and $R_4$ are each selected from the group consisting of H and OA, A is H or is selected from the group consisting of hydrocarbyl radicals,

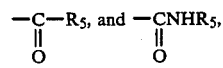

$R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, and pharmaceutically acceptable salts thereof. Preferably, $R_2$ is oxygen.
Preferably, $R_2$ is OA and A is H, and the compound is the (−) isomer.

37 Claims, No Drawings

METHOD AND COMPOSITIONS FOR TREATMENT OF PARKINSONISM SYNDROME IN MAMMALS

CROSS REFERENCE TO RELATED APPLICATIONS

This patent application is a continuation in part of U.S. patent application Ser. No. 640,685, filed on Aug. 13, 1984, and U.S. patent application Ser. No. 811,768, filed on Dec. 20, 1985, in the name of Alan S. Horn.

BACKGROUND OF THE INVENTION

1. Field of the Invention

This invention relates to methods of treating mammals to alleviate the symptoms of parkinsonism. This invention also provides compositions useful in such method.

2. Background of the Art

Parkinson's disease is a prevalent, serious neurological disease that afflicts approximately one-half million persons in the United States alone and more than 90 percent of the time the disease becomes manifest after the age of 55. There is no clear evidence that Parkinson's disease is determined by genetic factors and research is underway to discover possible environmental causes, such as infections or toxins.

Administration of one toxin, MPTP (N-methyl-4-phenyl-1,2,3,6-tetrahydropyridine), causes a syndrome that resembles Parkinson's disease when administered to primates. The MPTP-induced parkinsonism syndrome is similar to the idiopathic disease, both pathologically and biochemically, and it responds favorably to the administration of levo-dopa.

Toxic substances like MPTP may be widespread in the environment and there is concern that the accumulated effect of such toxins together with the effects of aging will contribute to development of parkinsonism. (Blume, E., "Street Drugs Yield Parkinson's model, JAMA, 1983, 250, 1314.)

Certain drugs which present the action of dopamine in the basal ganglia of the brain produce a parkinsonism-like syndrome as a side effect. For example, antipsychotic drugs such as the phenothiazines and butyrophenones block postsynaptic receptors for dopamine and cause symptoms that resemble parkinsonism. On the other hand, reserpine produces a parkinsonism-like condition by depleting dopamine available for release by the presynaptic neuron. Certain rare disorders, such as carbon monoxide or manganese poisoning, Wilson's disease and Shy-Drager syndrome, exhibit a parkinsonism-like syndrome as one aspect of a more widespread cerebral disorder.

Whatever its etiology, Parkinson's disease appears late in life and is characterized by loss of smooth control of voluntary muscles. Smooth control of voluntary movements is usually attributed to a balance of two neurotransmitters in the striatal tracts of the basal ganglia--dopaminergic components for inhibitory function, and cholinergic components for excitatory function. Imbalance in these individual systems produces disorders of movement and the disabilities of movement in parkinsonism are attributed to a deficiency in the dopaminergic component caused by the loss of neurons in the basal ganglia. By contrast the hyperkinesis characteristic of Huntington's chorea is thought to result from excessive dopaminergic activity in the basal ganglia. (Calne, D. B. "Parkinsonism, Clinical and Neuropharmacologic Aspects," *Postgrad. Med.*, 1978, 64, 82–88.)

Consequently, the goal of treatment fo parkinsonism is to balance striatal activity by reducing cholinergic activity or to augment dopaminergic function with centrally-active drugs levodopa or L-3,4-dihydroxyphenylalanine.

At present, for example, the most effective treatment of parkinsonism is achieved by levodopa, however many patients experience undesirable side effects such as nausea, vomiting, cardiac arrhythmias, abnormal involuntary movements and psychiatric disturbances. Therefore, there is a continuing search to find useful analogs of dopamine for the treatment of Parkinson's disease or the syndrome known as parkinsonism. Two known classes of dopamine analogs are the aporphines and the ergolines, and the need exists for novel and improved dopaminergic analogues capable of use in treating the symptoms of parkinsonism.

SUMMARY OF THE INVENTION

This invention provides a method for treating the symptoms of parkinsonism in mammals, e.g., humans, to reduce or reverse the symptoms of parkinsonism, which comprises administering to a mammal suffering from parkinsonism an effective amount of a compound selected from the group of racemic or optically active compounds represented by the general formula:

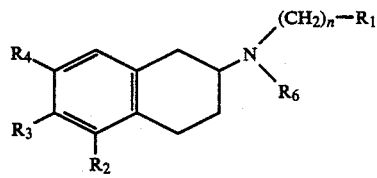

wherein $R_1$ is selected from the group consisting of organic radicals methyl, substituted or unsubstituted phenyls, pyridyl, hydroxyphenyl,

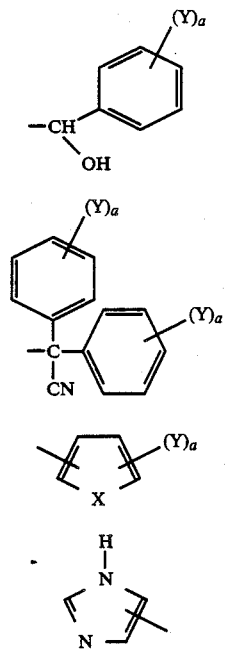

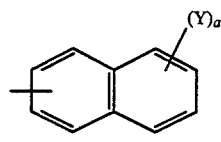

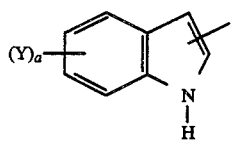

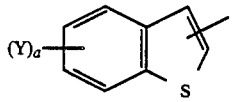

X is oxygen or sulfur,

Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, $R_2$, $R_3$ and $R_4$ are each selected from the group consisting of H and OA, A is H or is selected from the group consisting of hydrocarbyl radicals,

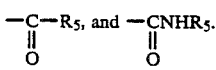

$R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, and pharmaceutically acceptable salts thereof. Preferably, $R_2$ is oxygen.

It is essential that the compound selected for use in the method of the present invention be an optically active compound or racemic mixture thereof capable of selectively activating the postsynaptic $D_2$ dopamine receptor, e.g., in a human. In particular, it is found that the (-) enantiomer of 5-hydroxy-2-(N-n-propyl-N-2-[2-thienyl]ethylamino)tetralin is especially preferred for use in the method of the present invention.

DETAILED DESCRIPTION OF THE INVENTION

The compounds used in the present invention are selected from the group of steroisomers or mixtures thereof of compounds represented by the general formula:

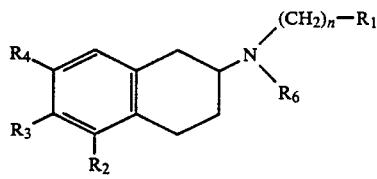

wherein $R_1$ is selected from the group consisting of organic radicals methyl, substituted or unsubstituted phenyls, pyridyl, hydroxyphenyl,

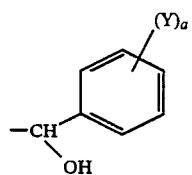

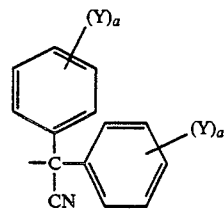

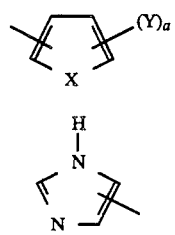

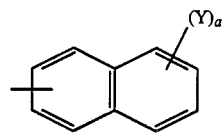

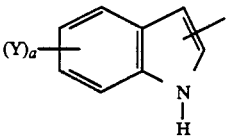

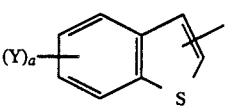

X is oxygen or sulfur,

Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from 0 to 3, R$_2$, R$_3$ and R$_4$ are each selected from the group consisting of H and OA, A is H or is selected from the group consisting of hydrocarbyl radicals,

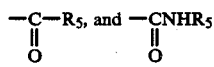

R$_5$ is selected from the group consisting of hydrocarbyl radicals; n is an integer between 1 and 3; and R$_6$ is an alkyl chain having between 1 and 3 carbon atoms with the provision that at least one of R$_2$, R$_3$ and R$_4$ is H, that at least one of R$_2$, R$_3$ and R$_4$ is not H, and that R$_2$ and R$_4$ are not both OA, and pharmaceutically acceptable salts thereof. Preferably, R$_2$ is oxygen.

A is preferably H or is selected from the group consisting of phenyl and alkyl radicals having from 1 to 12 carbon atoms, and more preferably R$^5$ is an alkyl or aryl radical that would serve to extend the activity of the compound in the body, for example phenyl, methyl t-butyl, d-methylphenyl, o-, m- or p-methoxyphenyl, or nonyl.

The more preferred groups represented by R$_1$ are thienyl, phenyl, hydroxyphenyl, furanyl and naphthalenyl, e.g., 2-thienyl, 3-thienyl, 3-hydroxyphenyl, 4-hydroxyphenyl, etc.

In the more preferred compounds for use in the present invention n is 2 and R$_2$ is OA; and most preferably A is H and R$_6$ is propyl.

It is essential that the compound selected for use in the method of the present invention be an optically active or racemic compound capable of selectively activating the postsynaptic dopamine D$_2$ receptor, e.g., in a human. In particular, it is found that the (−) isomer of 5-hydroxy-2-(N-n-propyl-N-2-[2-thienyl]ethylamino) tetralin is especially preferred for use in the method of the present invention.

The above compounds may be made by any of the methods disclosed in U.S. Pat. No. 4,564,628 entitled "Substituted 2-Aminotetralins," which is hereby incorporated by reference. A method for resolving the compounds into (+) and (−) isomers is disclosed in Example 1 hereinafter.

For purposes of this invention, designation of the (−) isomer shall mean that the (−) isomer is present in excess of the (+) isomer. Preferably, the mixture is greater than 90 mole percent of the (−) isomer. Most preferably, the (−) isomer is substantially pure, i.e., greater than 99 mole percent.

Particularly preferred compounds are as follows:

Compounds wherein R$_1$ is selected from the group consisting of radicals represented by the general formula:

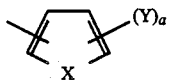

wherein X is oxygen or sulfur. Specific preferred compounds of this group include:
2-(N-n-propyl-N-2-[2-thienyl]ethylamino)-5-hydroxytetralin,
2-(N-n-propyl-N-2-[3-thienyl]ethylamino)-5-hydroxytetralin,
2-(N-n-propyl-N-2-[2-furanyl]ethylamino)-5-hydroxytetralin,
2-(N-n-propyl-N-2-[3-furanyl]ethylamino)-5-hydroxytetralin,
2-(N-n-propyl-N-2-[2-thienyl-4-methyl]ethylamino-5-hydroxytetralin,
2-(N-n-propyl-N-2-[2-thienyl-3,4,5-trimethyl]ethylamino)-5-hydroxytetralin,
2-(N-n-propyl-N-2-[2-thienyl-5-chloro]ethylamino)-5-hydroxytetralin,
2-(N-n-propyl-N-2-[2-(4-bromo-5-methyl)thienyl]ethylamino)-5-hydroxytetralin,
2-(N-n-propyl-N-2-[2-(4-methyl-5-ethyl)thienyl]ethylamino)-5-hydroxytetralin,
2-(N-n-propyl-N-2-[2-benzothienyl]ethylamino)-5-hydroxytetralin and
2-(N-n-propyl-N-2-[3-benzothienyl]ethylamino)-5-hydroxytetralin.

Compounds wherein R$_1$ is selected from the group of radicals represented by the general formulae:

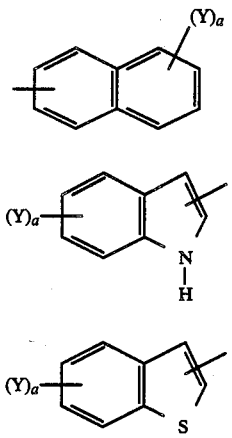

wherein Y and a are as defined above. More preferably, Y comprises no more than 5 carbon atoms and a is 0 or 1. Specific preferred compounds of this group include:
2-(N-n-propyl-N-2-[2-naphthalenyl]ethylamino)-5-hydroxytetralin,
2-(N-n-propyl-N-2-[4-indolyl]ethylamino)-5-hydroxytetralin,
2-(N-n-propyl-N-2-[2-benzothienyl]ethylamino)-5-hydroxytetralin,
and
2-(N-n-propyl-N-2-[3-benzothienyl]ethylamino)-5-hydroxytetralin;

Compounds wherein R$^1$ is phenyl and/or substituted phenyl and is selected from the group of radicals represented by the general formula:

wherein Y and a are as defined above. Specific preferred compounds of this group include:
2-(N-n-propyl-N-2-[phenyl]ethylamino)-5-hydroxytetralin,
2-(N-n-propyl-N-2-[4-hydroxyphenyl]ethylamino)-5-hydroxytetralin,
and
2-(N-n-propyl-N-2-[3-hydroxyphenyl]ethylamino)-5-hydroxytetralin;

This invention provides a method of treatment of the symptoms of parkinsonism which comprises administering a therapeutically effective amount of one of the foregoing compounds to a patient suffering such symptoms. Even more preferably, the method of the present invention comprises administering the (−) isomer of 5-hydroxy-2-(N-n-propyl-N-2-[2-thienyl]ethylamino)-tetralin to a human or other mammal to reduce the symptoms of parkinsonism.

Parkinsonism, as used herein, signifies a condition characterized by the symptoms to which the term Parkinson's disease refers—tremor, bradykinesia, rigidity, and a disturbance of posture. As used herein, "tremor" refers to the rhythmically alternating contractions (usually three to five per second) of a muscle group and its antagonist. Tremor often disappears on purposeful movement and usually increases remarkably with anxiety or stress. "Bradykinesia," as used herein, is characterized by decreased control in spontaneous movement, loss of normal associated movements, and slow initiation of all voluntary movements. "Rigidity" as used herein, is an intermittent resistance to passive movement of extremities that is often characterized as a "cogwheel" or "ratchet" resistance. In general, a pharmacologically-effective daily dose can be from 0.01 mg./kg. to 100 mg./kg. per day, bearing in mind, of course, that in selecting the appropriate dosage, in any specific case, consideration must be given to the patient's weight, general health, metabolism, age and other factors which influence response to the drug. A particularly preferred dose is 1.0 mg./kg. per day.

Another embodiment of this invention is the provision of pharmaceutical compositions in dosage unit form which comprise from about 2 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients can be, for example, inert diluents, for example calcium carbonate, sodium carbonate, lactose, calcium phosphate, or sodium phosphate; granulating and disintegrating agents, for example maize starch, or alginic acid; binding agents, for example starch, gelatine, or acacia; and lubricating agents, for example magnesium stearate, stearic acids, or talc. The tablets can be uncoated or they can be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate, or kaolin, or as soft gelatin capsules wherein the active ingredient is mixed with an oil medium, for example archis oil, liquid paraffin, or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gum acacia; dispersing or wetting agents may be naturally-occurring phosphatides, for example lecithin, or condensation products of an alkylene oxide with fatty acids, for example polyoxethylene stearate, or condensation products of ethylene oxide with long chain aliphatic alcohols, for example heptadecethyleneoxy-cetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, n-propyl, or p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents may also be present.

Syrups and elixirs may be formulated with sweetening agents, for example glycerol, sorbitol or sucrose. Such formulations may also contain a demulcent, preservative, flavoring and coloring agents. The pharmaceutical compositions may be in the form of a sterile injectable preparation, for example as serile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol.

The pharmaceutical compositions may be tableted or otherwise formulated so that for every 100 parts by weight of the composition there are present between 5 and 95 parts by weight of the active ingredient. The dosage unit form will generally contain between about 1 mg. and about 100 mg. of the active ingredient of the formula stated above.

From the foregoing discussion of formulations it is apparent that the compositions of this invention can be administered orally or parenterally. The term parenteral as used herein includes subcutaneous injection, intravenous, intramuscular, or intrasternal injection or infusion techniques. The compositions can also be administered transdermally by topical administration to skin and mucosal membranes.

To illustrate the manner in which the invention may be carried out, the following examples are given. It is understood, however, that the examples are for the purpose of illustration and the invention is not to be regarded as limited to any of the specific materials or conditions therein.

Animal test models for evaluating postsynaptic dopaminergic receptor function in the central nervous system were used to compare the effects of the (+) and (-) stereoisomers of 5-hydroxy-2-(N-n-propyl-N-2-[2-thienyl]ethylamino)tetralin (N-0437). It is believed that it is desirable for the treatment of parkinsonism that the dopaminergic agent selectively activate the postsynaptic receptor.

EXAMPLE 1

Racemic 2-(N-n-propylamino)-5-methoxytetralin was resolved into its (−) and (+) isomers according to the method of Ten Hoeve and Wynberg (J. Org. Chem. 1985, 50, 4508), using the (+) isomer of 4-(2-chlorophenyl)-5,5-dimethyl-2-hydroxy-1,3,2-dioxaphosphorinane 2-oxide.

6.23 gm. (28.5 mmol) of racemic 2-(N-n-propylamino)-5-methoxytetralin and 7.7 gm. (27.8 mmol) of (+) 4-(2-chlorophenyl)-5,5-dimethyl-2-hydroxy-1,3,2-dioxaphosphorinane 2-oxide were dissolved by warming in 33 ml. of absolute alcohol and 10 ml. of water. The heating was discontinued and the solution was allowed to cool while being stirred. After 15 min., the mixture was filtered off and washed with ether to yield 6.08 gm. of the salt (12.27 mmol, 43%). The salt was then stirred 30 min. with a solution of sodium hydroxide dissolved in 75 ml. water to which was added 25 ml. chloroform. After mixing, this was extracted with 2×50 ml. portions of chloroform. The organic extracts were washed with water, dried over magnesium sulfate and evaporated to dryness to yield 2.66 gm. (99%) of a slightly colored oil. The optical rotation for 49 mg. in 5 ml. of methanol was −62.4° (578 nm). (The (+) isomer can be similarly isolated by using (−) 4-(2-chlorophenyl)-5,5-dimethyl-2-hydroxy-1,3,2-dioxaphosphorinane 2-oxide.)

The resultant isomers of 2-(N-n-propylamino)-5-methoxytetralin are then converted to (+) and (−) 5-hydroxy-2-(N-n-propyl-N-2-[2-thienyl]ethylamino)-tetralin by the methods described in U.S. Pat. No. 5,564,628 herein incorporated by reference.

The pharmacological activities of the (+) and (−) stereoisomers were determined by examining their ability to displace the specific D-2 dopamine receptor binding of a tritium-containing racemic mixture of 5-hydroxy-2-(N-n-propyl-N-2-[2-thienyl]ethylamino)tetralin to homogenates of calf brain corpus striatum. In this preparation, which is a modification of the one reported by Mulder et al. "Kinetic and Pharmacological Profiles of the In-Vitro Binding of the Potent Dopamine Agonist $^3$H-N,N-dipropyl--5,6-dihydroxy-2-Aminotetralin to Rat Striatal Membranes," Eur. J. Pharmacol. 112 (1985) 73–79, for rat brain corpus striatum, the tritium-containing racemic mixture had an affinity constant ($K_d$) of 1.6 nanomoles and a $\beta$max of 26.0 picomoles/gm, and has a known high affinity for the post-synaptic receptors. The IC$_{50}$ values (i.e., the concentration of drug required to inhibit the binding of labelled drug by 50 percent) for the (−) and (+) isomers were 0.5 and 71.0 nanomolar, respectively. Thus the (−) isomer is 140 times more potent than the (+) isomer for binding to the postsynaptic receptors.

EXAMPLE 2

Turning behavior in 6-hydroxydopamine lesioned rats

Rotation after 6-hydroxy dopamine (6-OHDA) lesions have been induced was tested in male rats. 6-OHDA (dissolved in 1 μl of 0.9% NaCl) was injected into the substantia nigra at coordinates A-1.8, L-1.9, V-2.0 (Kong and Klippel, The Rat Brain, a Stereotoxic Atlas of the Forebrain and Lower Parts of the Brain Stem (The Williams and Wilkins Company, Baltimore, 1963). To select a successfully denervated animal, rats were tested twice with intraparenteral injections of apomorphine at a dose of 0.5 mg/kg of body weight at a 10 days interval. Rotational behavior was recorded in rotometers according to the method of Ungerstedt and Arbuthnott (1970), "Quantitative Recording of Relational Behavior in Rats after 6-hydroxydopamine Lesions of the Nigrostriatal Dopamine System," Brain Res. 29, 485.

Comparison with apomorphine of (+) and (−) isomers of N-0437 at doses of 1 and 10 μmol/kg is summarized in Table 2. The same contralateral turning as caused by apomorphine was caused by (−) N-0437, while (+) N-0437 up to a dose of 10 μmol/kg failed to produce significant contralateral rotation. Thus, (−) N-0437 showed significant activity in this postsynaptic dopamine receptor model while (+) N-0437 showed no effect, thereby showing that the postsynaptic dopamine D$_2$ receptors may be selectively activated.

TABLE 2

| Compound | No. Animals Tested | Dose μmol/kg | Net Number of Contralateral Turns ± S.E.M. |
|---|---|---|---|
| Saline | 4 | 0 | 0 ± 4 |
| Apomorphine | 10 | 1 | 240 ± 22 |
| (+) N-0437 | 5 | 1 | 0 ± 5 |
| (+) N-0437 | 6 | 10 | 3 ± 2 |
| (−) N-0437 | 5 | 1 | 278 ± 39 |
| (−) N-0437 | 5 | 10 | 201 ± 25 |
| (±) N-0437 | 4 | 1 | 171 ± 32 |

Stereotyped Behavior in rats

Stereotyped behaviors such as continuous gnawing, biting, licking, are observed following stimulation of postsynaptic dopamine receptors. (Ernst, A.M., 1967, Psychopharmacologia, 10:316). The method of van der Weide, J. et al (1986, Eur. J. Pharmacol., 125:273–282) was used to assess the intensity of stereotyped behavior in male rats injected i.p. with either (−) N-0437 or (+) N-0437. Male rats were injected intraparenterally with either (+) or (−) N-0437 and placed separately in cages. Stereotyped behavior was assessed and scored in semi-darkness every 5 minutes using the scoring system of Costal, et al., "Differential Activation by some 2-aminotetralin Derivatives of the Receptor Mechanisms in the Nucleus Accumbens of Rats Which Mediate Hyperactivity and Stereotyped Biting," European J. Pharmacol. (1977), 41, 307. (−) N-0437 produced a half maximal effect at 1.7 μmol/kg. However, (+) N-0437 was inactive in this test for postsynaptic dopamine receptor activity at doses up to 100 μg/kg.

EXAMPLE 3

The dopamine agonist apomorphine and the stereoisomers of N-0437 were examined for their ability to inhibit the calcium-dependent release of [$^3$H]ACh from rabbit striatal slices labelled with [$^3$H]choline, a known in vitro test for post synaptic dopamine D$_2$ receptor agonists. Striata were sliced with a tissue chopper incubated for 20 minutes at 37° C. in Krebs solution, composed of (in mM): Nacl, 108; Kcl, 4.7; glucose, 11.1;

NaHCO$_3$, 25; Mgcl$_2$, 1.2; NaH$_2$, PO$_4$, 1.0; Cacl$_2$, 1.3; ascorbic acid, 0.11; and Na$_2$EDTA, 0.004, that contained 0.1 μM 3H-choline. The tissues were washed and individual slices were placed in glass superfusion chambers containing two platinum electrodes 30 mm apart. The tissues were superfused with Krebs solution at a rate of 1 ml/minute until the spontaneous outflow of radioactivity leveled off. $^3$H-acetyl-choline release was induced by field stimulation of 3HZ, 2 msec duration at a current of 20 mA. Samples were collected before, during, and after stimulation. Two periods of stimulation were used; test drugs were present during the second stimulation. Released radioactivity was determined by liquid scintillation counting.

The percent of total tissue radioactivity released by electrical stimulation above the spontaneous levels of release was 3.59±0.12% (n=3) and the ratio S$_2$/S$_1$ was 0.95±0.03 (n=3). Apomorphine (0.1uM) and (−) N-0437 (0.01μM inhibited by about 50% the calcium-dependent release of [$^3$H]ACh elicited by electrical stimulation from rabbit striatal slices. The (+) isomer at a concentration of (0.1μM) almost completely antagonized the inhibition of calcium-dependent release of [$^3$H]ACh elicited by apomorphine (0.10μM) and (−) N0437 (0.0182 M).

EXAMPLE 4

Common marmosets were treated with sufficient MPTP to cause motor deficits: animals of either sex (weight range (289–390g) were treated with 1-methyl-4-phenyl-1,2,3,6-tetrahydropyridine (MPTP) in single doses of 1-2 mg/kg ip daily. Since the individual response of animals differed markedly, a variable dose regime was employed so as to render them parkinsonian. Following cessation of MPTP administration, animals were allowed several week to recover from the acute effects of MPTP treatment. There was a dosedependent reversal of motor deficits following both intraperitoneal injection of (−) N-0437 at dosages of 0.1, 0.3, 0.5 and 0.7 mg/kg or oral administration at dosages of 0.1, 0.3, 0.63 and 1.25 mg/kg of a racemic mixture of N-0437.

To test the effect of topical application, the (-) and (+) stereoisomers of N-0437 were separately administered to MPTP treated marmosets by applying the isomers topically to the skin in alcoholic solutions. Twenty-four hours after application of the (−) isomer, the motor deficits induced by MPTP were clearly improved. Movements were faster, more coordinated, and less clumsy as determined by visual inspection. Measurement of locomotor activity in photocell cages showed the number of light beam interruptions was almost restored to control levels up to 32 hours after application of (−) N-0437. Animals treated with the (+) enantiomer showed neither a behavioral improvement nor a stimulation of locomotor activity.

While particular embodiments of the invention have been described, it will be understood, of course, that the invention is not limited thereto since many obvious modifications can be made and it is intended to include within this invention any such modifications as will fall within the scope of the appended claims. For example, this invention may be used to treat other diseases that are believed to involve dopaminergic response such as those treated by depressing prolactin levels, e.g., hyperprolactinemia and breast cancer.

Having now described The invention, I claim:

1. A method for treating the symptoms of parkinsonism in a mammal comprising administering to said mammal an effective amount of one or more compounds selected from the group consisting of the optically active or racemic compounds wherein the amount of the negative isomer is an amount effective to treat parkinsonism said compounds being represented by the formula:

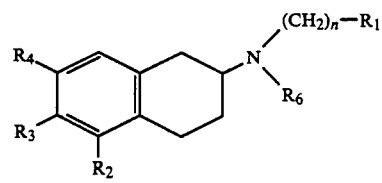

wherein
R$_1$ is

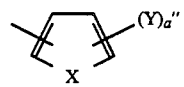

X is sulfur,
Y is hydroxy, and a is an integer of from zero to 3,
R$_2$, R$_3$ and R$_4$ are each selected from the group consisting of H and OA, A is H or is selected from the group consisting of hydrocarbyl radicals,

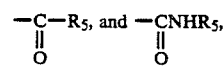

R$_5$ is selected from the group consisting of hydrocarbyl radicals; n is an integer between 1 and 3; and R$_6$ is an alkyl chain having between 1 and 3 carbon atoms with the provision that at least one of R$_2$, R$_3$ and R$_4$ is H, that at least one of R$_2$, R$_3$ and R$_4$ is not H, and that R$_2$ and R$_4$ are not both OA, and pharmaceutically acceptable salts thereof.

2. The method of claim 1 wherein Y is zero and R$_2$ is oxygen.

3. The method of claim 2 wherein A is selected from the group consisting of phenyl and alkyl radicals having from 1 to 12 carbon atoms.

4. The method of claim 3 wherein R$_5$ is selected from the group of alkyl or aryl radicals.

5. The method of claim 4 wherein n is 2.

6. The method of claim 5 wherein R$_2$, R$_3$ and R$_4$ are selected from the group consisting of H and OA wherein A is H,

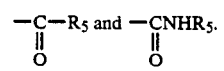

7. The method of claim 6 wherein said R$_1$ is selected from the group consisting of 2-thienyl and 3-thienyl.

8. The method of claim 7 wherein R$_4$ and R$_3$ are H and R$_2$ is OH.

9. The method of claim 8 wherein R$_1$ is 2-thienyl and said mammal is a human.

10. The method of claim 1 wherein the compound is the optically active compound.

11. The method of claim 9 wherein the compound is the optically active compound.

12. The method of claim 11 wherein the optically active compound is the (−) isomer.

13. The method of selectively activating the postsynaptic $D_2$ dopamine receptors of a mammal, comprising administering to said mammal an effective amount of one or more compounds selected from the group consisting of optically active or racemic compounds wherein the amount of the negative isomer is an amount effective to treat parkinsonism, said compounds being represented by the formula:

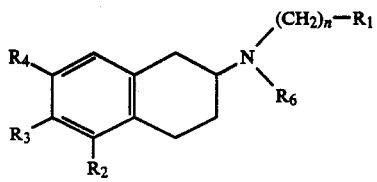

wherein
$R_1$ is

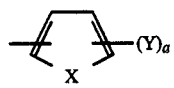

X is sulfur,
Y is hydroxy, and a is an integer of from zero to 3,
$R_2$, $R_3$ and $R_4$ are each selected from the group consisting of H and OA, A is H or is selected from the group consisting of hydrocarbyl radicals,

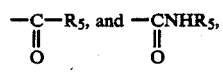

$R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, and pharmaceutically acceptable salts thereof.

14. The method of claim 13 wherein Y is zero, and $R_2$ is oxygen.

15. The method of claim 14 wherein A is selected from the group consisting of phenyl and alkyl radicals having from 1 to 12 carbon atoms.

16. The method of claim 15 wherein $R_5$ is selected from the group of alkyl or aryl radicals.

17. The method of claim 16 wherein n is 2.

18. The method of claim 17 wherein $R_2$, $R_3$ and $R_4$ are selected from the group consisting of OA and wherein A is H,

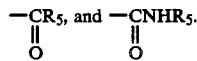

19. The method of claim 18 wherein said $R_1$ is selected from the group consisting of 2-thienyl and 3-thienyl.

20. The method of claim 19 wherein $R_4$ and $R_3$ are H and $R_2$ is OH.

21. The method of claim 20 wherein $R_1$ is 2-thienyl and said mammal is a human.

22. The method of claim 13 wherein the compound is the optically active compound.

23. The method of claim 21 wherein the compound is the optically active compound.

24. The method of claim 23 wherein the optically active compound is the (−) isomer.

25. A method for treating the symptoms of diseases involving dopaminergic response which comprises administering to a patient having the disease an effective amount wherein the amount of the negative isomer is an amount effective to treat the disease of one or more compounds selected from the group consisting of the isomers of optically-active or racemic compounds represented by the general formula:

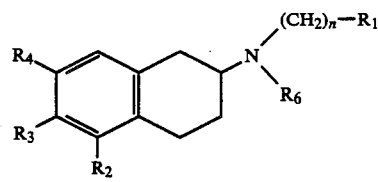

wherein
$R_1$ is

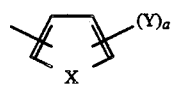

X is sulfur, Y is hydroxy, and a is an integer of from zero to 3,
$R_2$, $R_3$ and $R_4$ are each selected from the group consisting of H and OA, A is H or is selected from the group consisting of hydrocarbyl radicals,

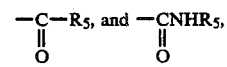

$R_5$ is selected from the group consisting of hydrocarbyl radicals; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, and pharmaceutically are not both OA, and pharmaceutically acceptable salts thereof.

26. The method of claim 25 wherein a is zero and $R_2$ is oxygen.

27. The method of claim 26 wherein A is selected from the group consisting of phenyl and alkyl radicals having from 1 to 12 carbon atoms.

28. The method of claim 27 wherein A is selected from alkyl radicals having from 1 to 3 carbon atoms.

29. The method of claim 28 wherein n is 2.

30. The method of claim 18 wherein $R_2$, $R_3$ and $R_4$ are selected from the group consisting of OA wherein A is hydrogen, and

or

31. The method of claim 25 wherein said $R_1$ is selected from the group consisting of 2-thienyl and 3-thienyl.

32. The method of claim 26 wherein $R_4$ and $R_3$ are H and $R_2$ is OH.

33. The method of claim 26 wherein $R_1$ is 2-thienyl and said mammal is a human.

34. The method of claim 25 wherein the compound is the optically active compound.

35. The method of claim 31 wherein the compound is the optically active compound.

36. The method of claim 35 wherein the optically active compound is the (−) isomer.

37. The method of claim 19 wherein said disease is hyperprolactinemia.

* * * * *